(12) United States Patent
Truong et al.

(10) Patent No.: US 11,931,544 B2
(45) Date of Patent: *Mar. 19, 2024

(54) BOLUS DELIVERY DEVICE

(71) Applicant: Avent, Inc., Alpharetta, GA (US)

(72) Inventors: Hector Dung Truong, Westminster, CA (US); Justin J. Coker, Laguna Niguel, CA (US); Paul D. Jun, La Crescenta, CA (US)

(73) Assignee: Avent, Inc., Alpharetta, GA (US)

( * ) Notice: Subject to any disclaimer, the term of this patent is extended or adjusted under 35 U.S.C. 154(b) by 143 days.

This patent is subject to a terminal disclaimer.

(21) Appl. No.: 17/694,150

(22) Filed: Mar. 14, 2022

(65) Prior Publication Data

US 2022/0193328 A1 Jun. 23, 2022

Related U.S. Application Data

(63) Continuation of application No. 16/618,583, filed as application No. PCT/US2018/028112 on Apr. 18, 2018, now Pat. No. 11,273,254.

(Continued)

(51) Int. Cl.
*A61M 5/142* (2006.01)
*A61M 5/145* (2006.01)
(Continued)

(52) U.S. Cl.
CPC ........ *A61M 5/1424* (2013.01); *A61M 5/1454* (2013.01); *A61M 5/152* (2013.01);
(Continued)

(58) Field of Classification Search
CPC .. A61M 5/1424; A61M 5/1454; A61M 5/152; A61M 2005/1405; A61M 2205/0216
See application file for complete search history.

(56) References Cited

U.S. PATENT DOCUMENTS 6,206,850 B1  3/2001  O'Neil
6,416,495 B1  7/2002  Kriesel et al.
(Continued)

FOREIGN PATENT DOCUMENTS

JP   2011125433 A   6/2011
WO   2002098493 A1  12/2002
(Continued)

OTHER PUBLICATIONS

International Search Report and Written Opinion, dated Jul. 3, 2018, received in connection with International Patent Application No. PCT/US2018/028112.

(Continued)

*Primary Examiner* — Laura A Bouchelle
*Assistant Examiner* — John A Doubrava
(74) *Attorney, Agent, or Firm* — Meunier Carlin & Curfman LLC

(57) ABSTRACT

A bolus delivery device is provided that comprises a housing and a reservoir defined by an activation dome and a reservoir seat and disposed within the housing for receipt of a volume of a fluid. The bolus delivery device further comprises a bladder disposed in the housing that is in fluid communication with the reservoir for receipt of the fluid from the reservoir; an actuator; an inlet conduit in fluid communication with the reservoir for providing the fluid to the reservoir; and an outlet conduit in fluid communication with the bladder for providing the fluid to a patient. The actuator is in operative communication with the reservoir to initiate a flow of the fluid from the reservoir to the bladder. The bladder expands as the bladder receives the fluid and contracts as the bladder dispenses the fluid. An infusion assembly including a bolus delivery device also is provided.

20 Claims, 9 Drawing Sheets

Related U.S. Application Data

(60) Provisional application No. 62/516,165, filed on Jun. 7, 2017.

(51) Int. Cl.
    *A61M 5/152*     (2006.01)
    *A61M 5/14*     (2006.01)

(52) U.S. Cl.
    CPC ............... *A61M 2005/1405* (2013.01); *A61M 2205/0216* (2013.01)

(56) References Cited

U.S. PATENT DOCUMENTS

| | | | |
|---|---|---|---|
| 8,308,688 B2 | 11/2012 | Valle | |
| 11,273,254 B2 * | 3/2022 | Truong | ............... A61M 5/1413 |
| 2012/0253283 A1 * | 10/2012 | Yamada | ............ A61M 5/16809 |
| | | | 604/131 |
| 2017/0106137 A1 * | 4/2017 | Lee | ......................... A61M 5/30 |

FOREIGN PATENT DOCUMENTS

| | | |
|---|---|---|
| WO | 2004060453 A1 | 7/2004 |
| WO | 2012080862 A2 | 6/2012 |
| WO | 2017013124 A1 | 1/2017 |
| WO | 2017099999 A1 | 6/2017 |

OTHER PUBLICATIONS

Office Action, dated Jan. 22, 2022, received in connection with corresponding JP Patent Application No. 2019-567288.

\* cited by examiner

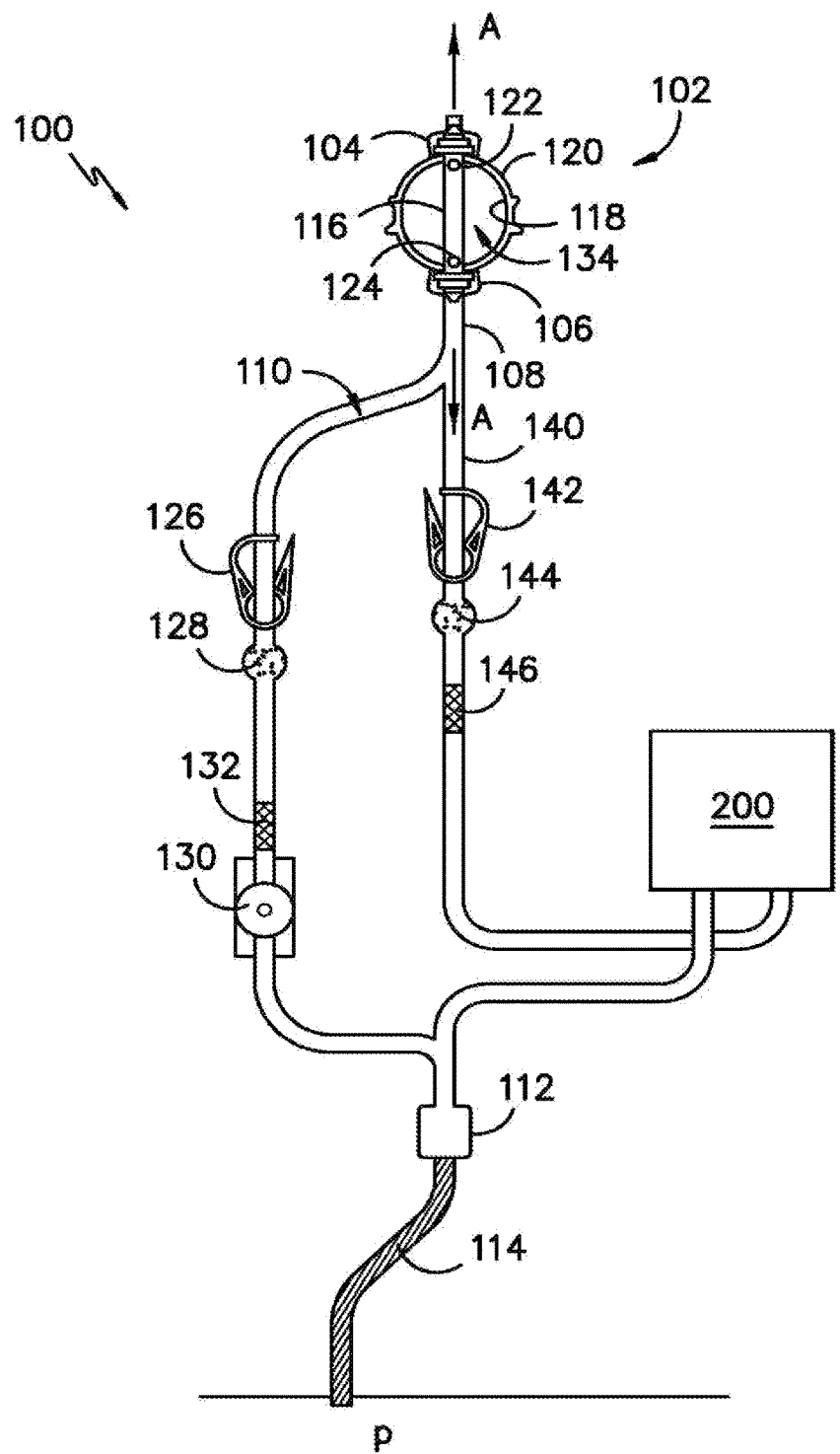
FIG. -1-

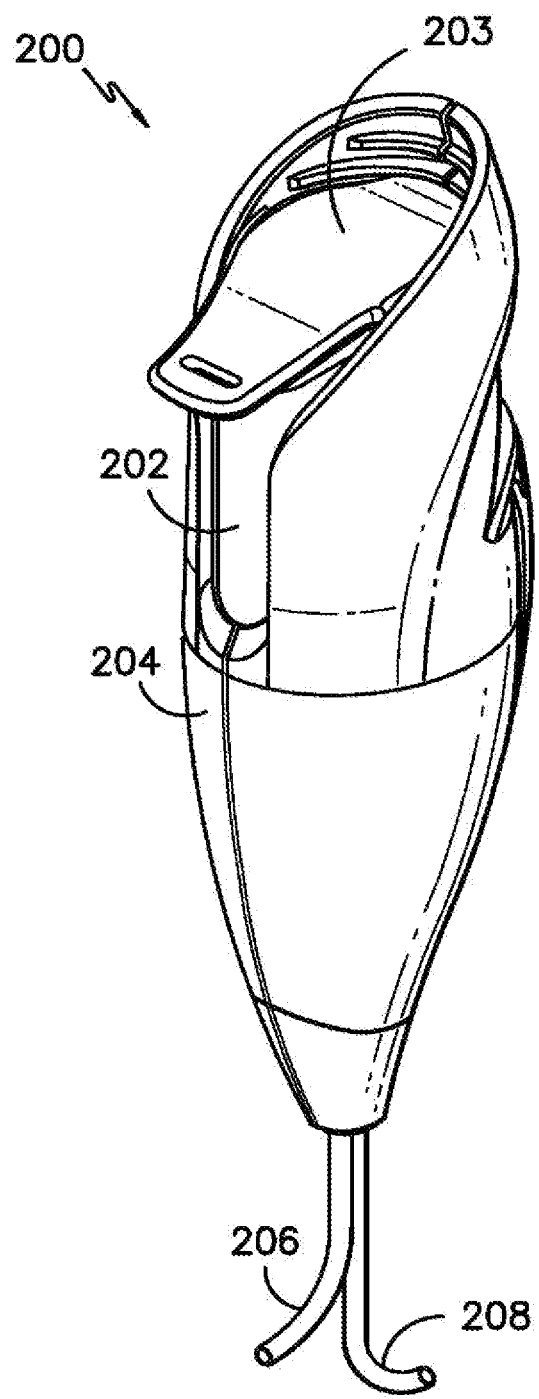
FIG. -2-

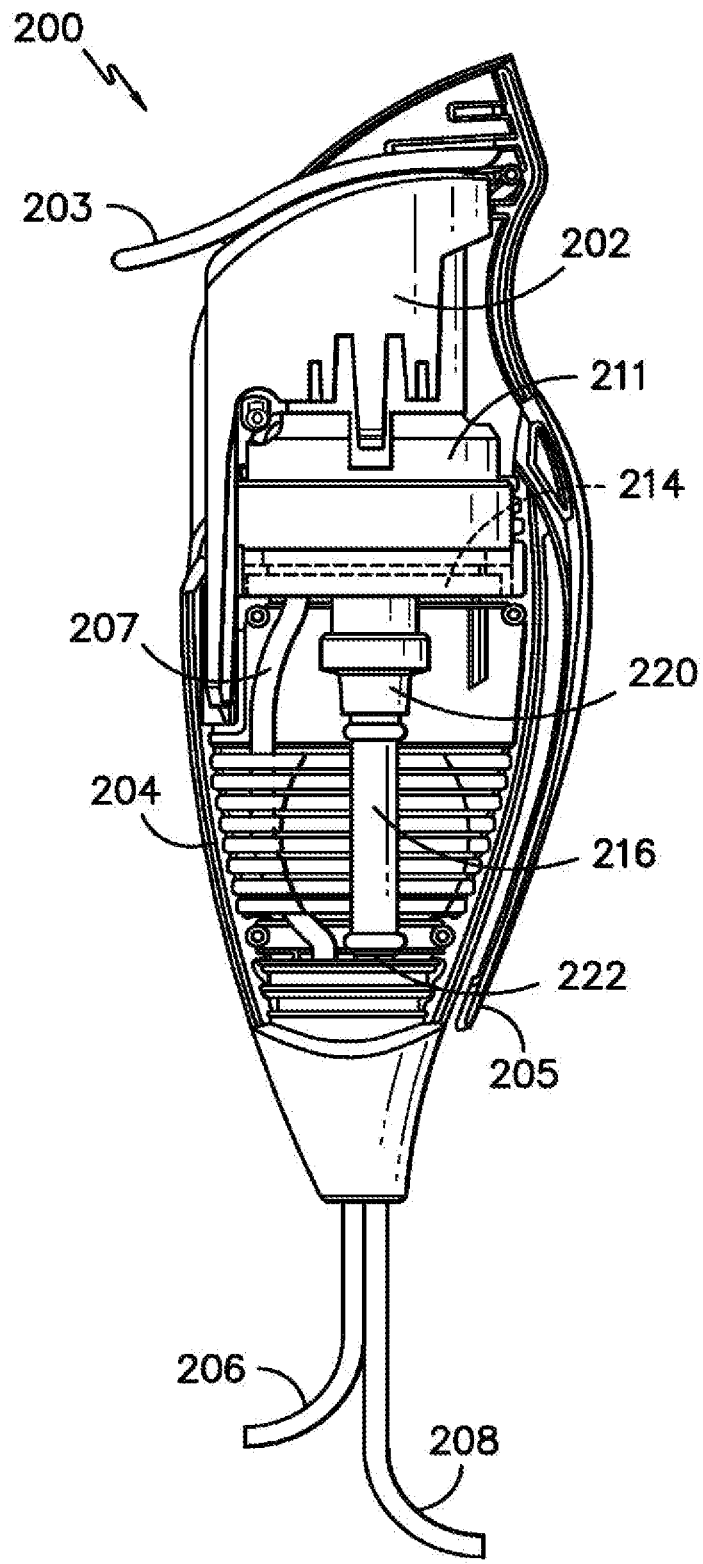
FIG. -3A-

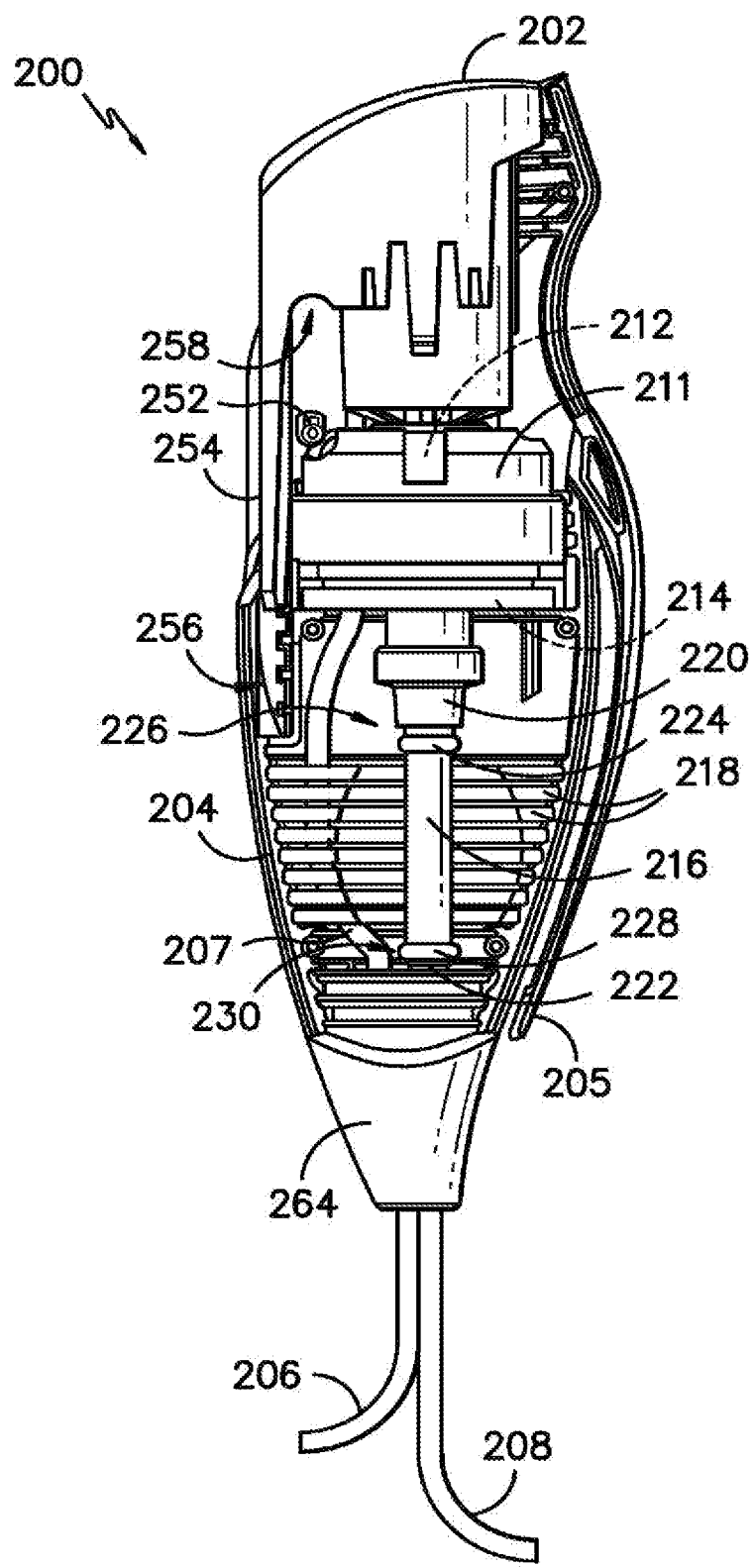
FIG. -3B-

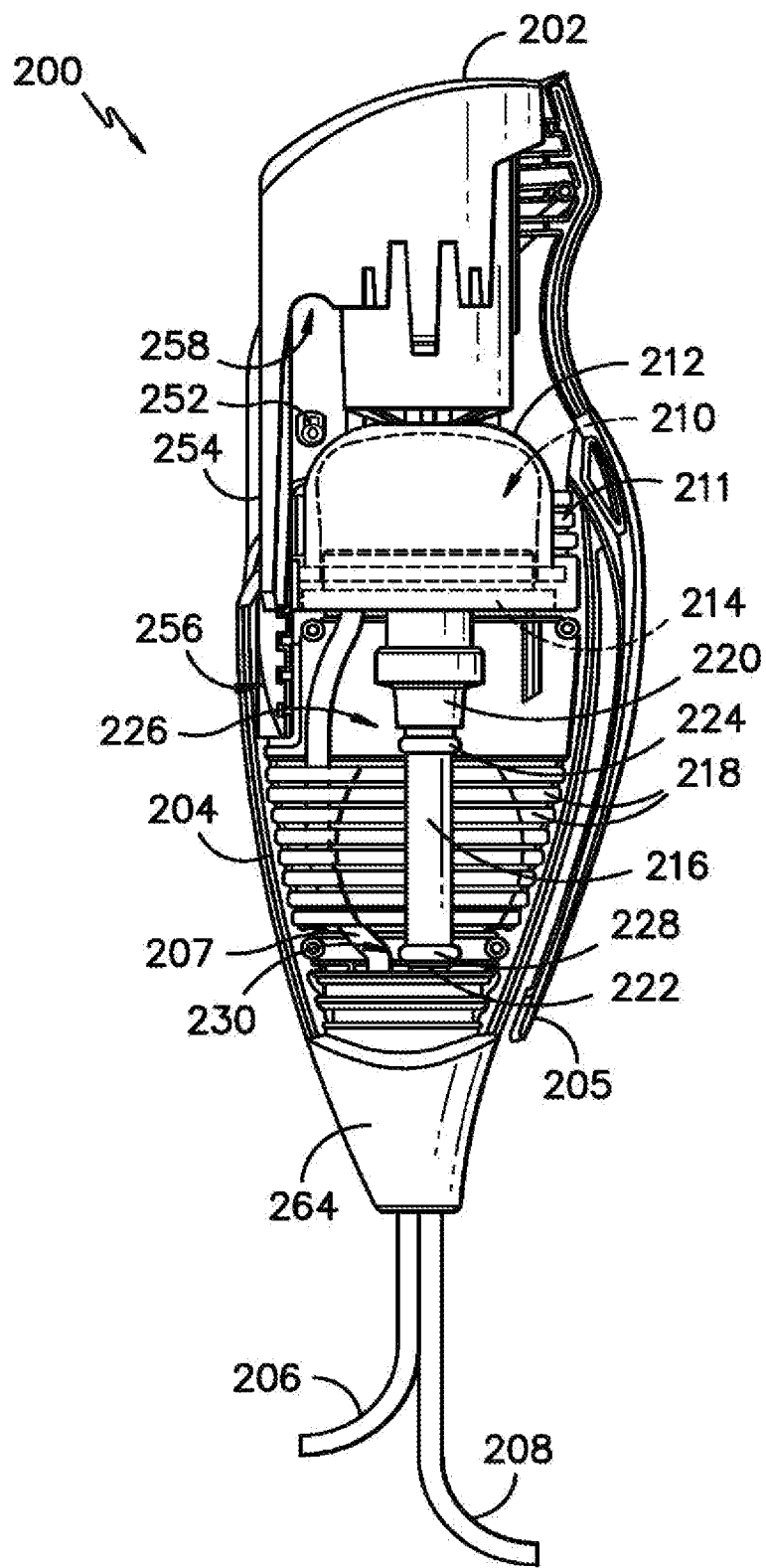
FIG. -3C-

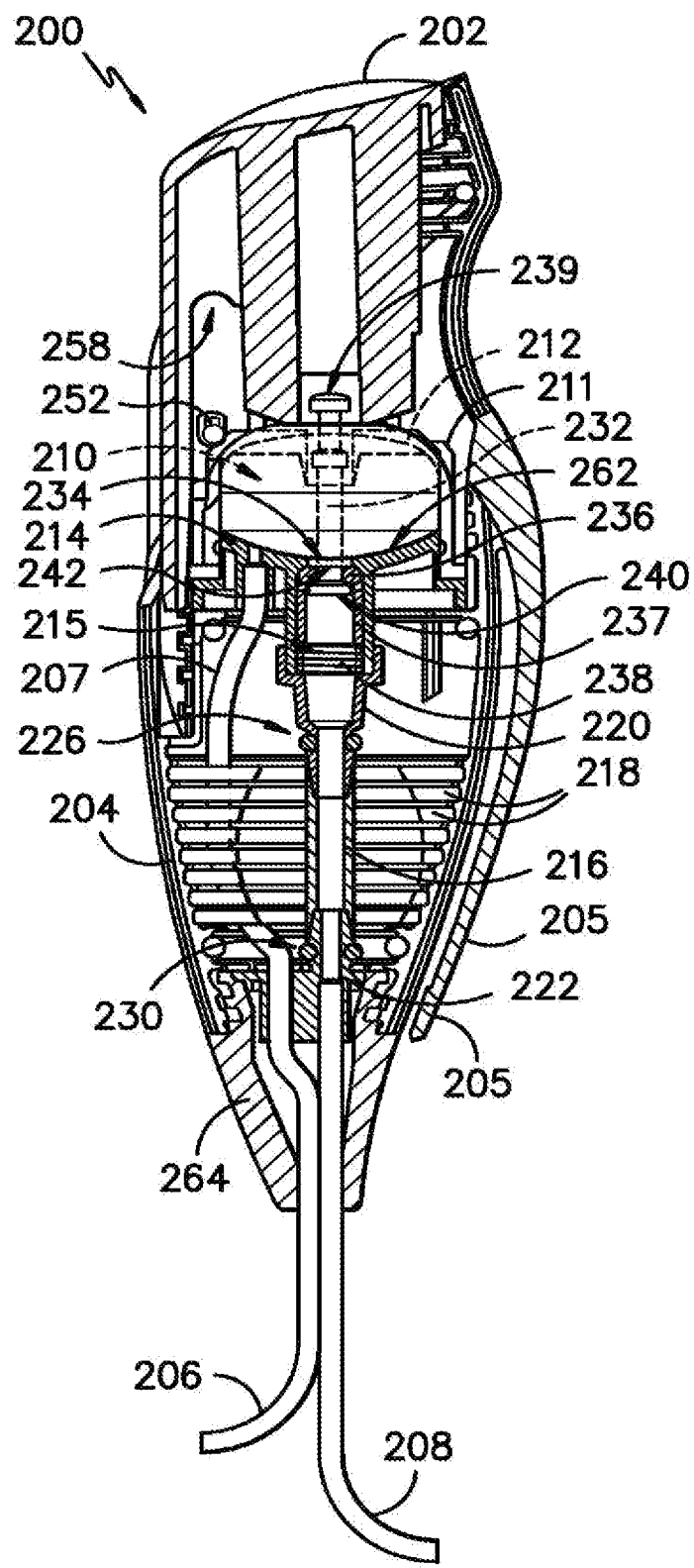
FIG. -4-

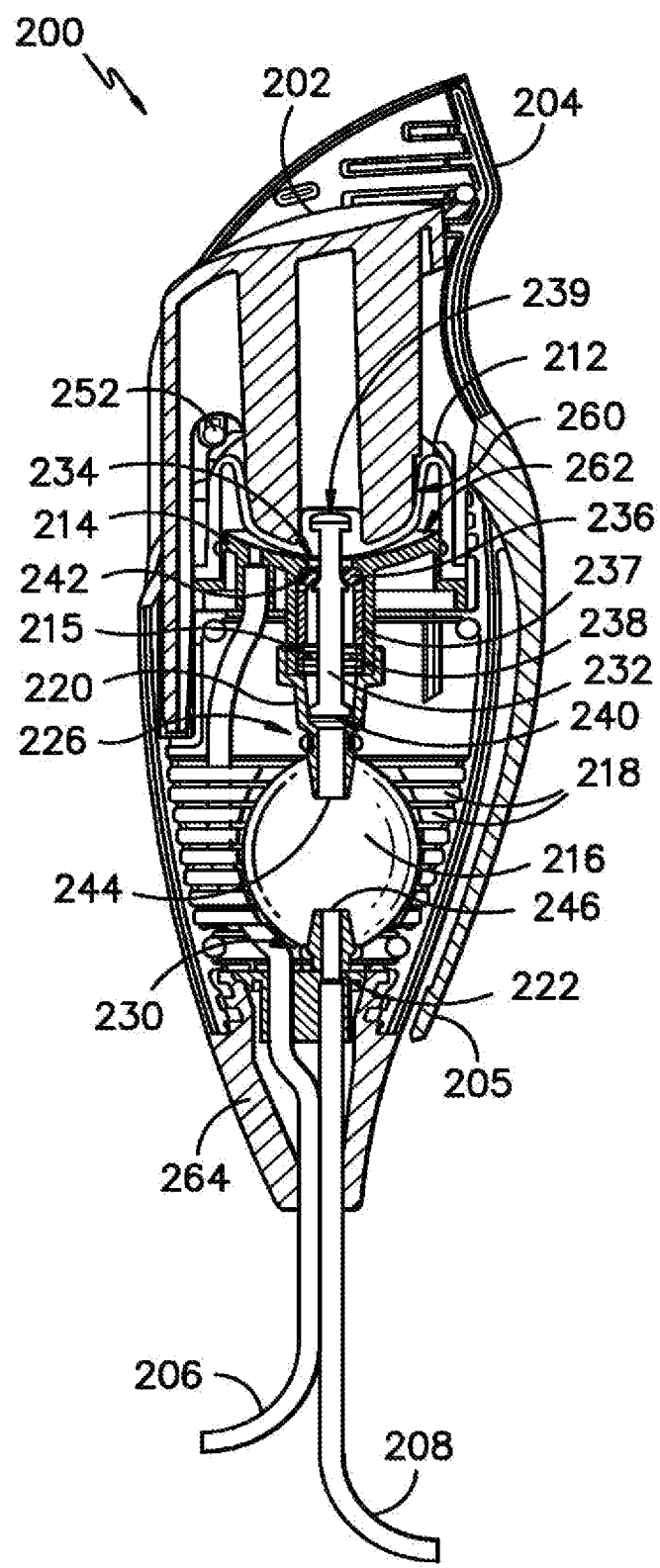
FIG. -5-

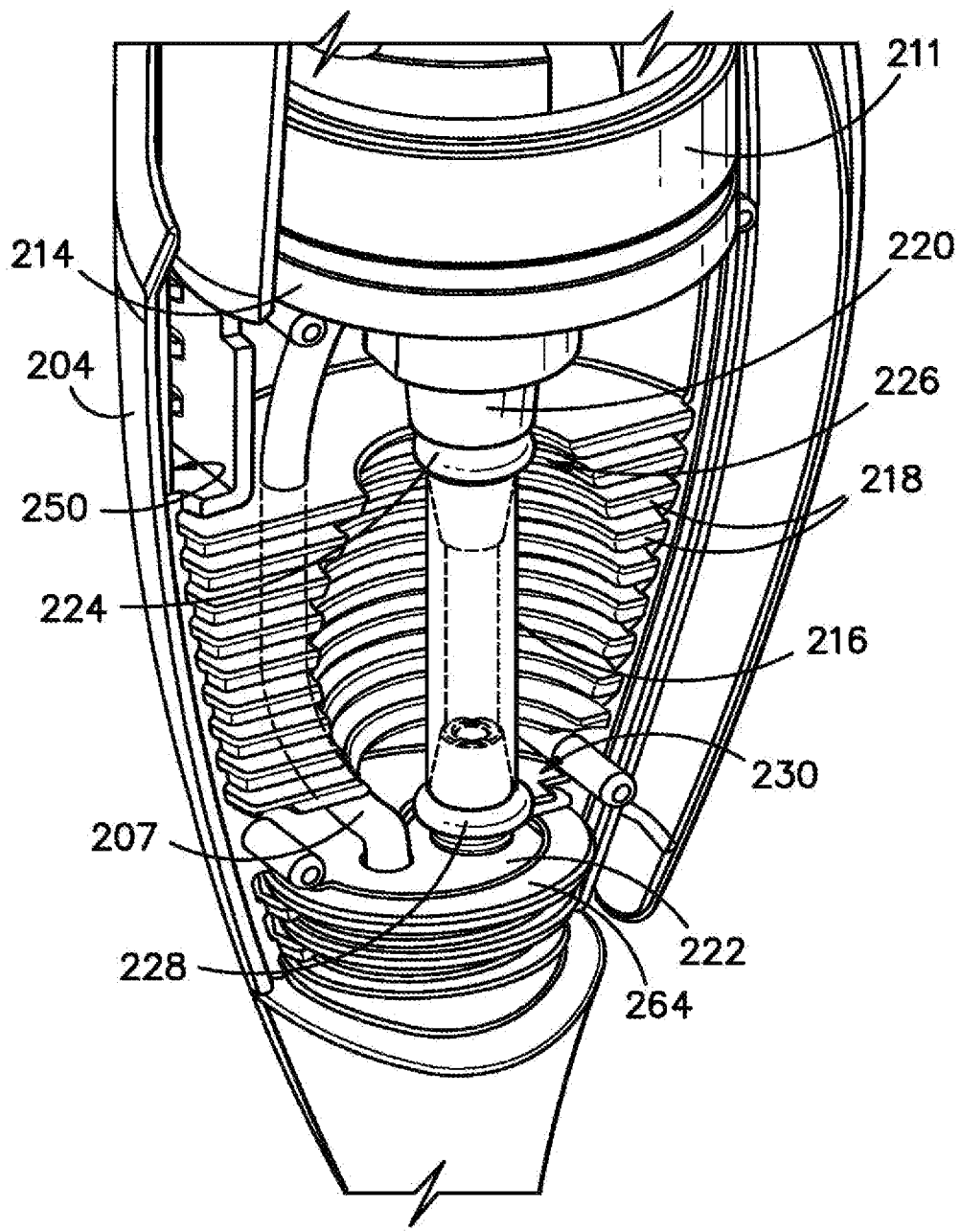
FIG. -6-

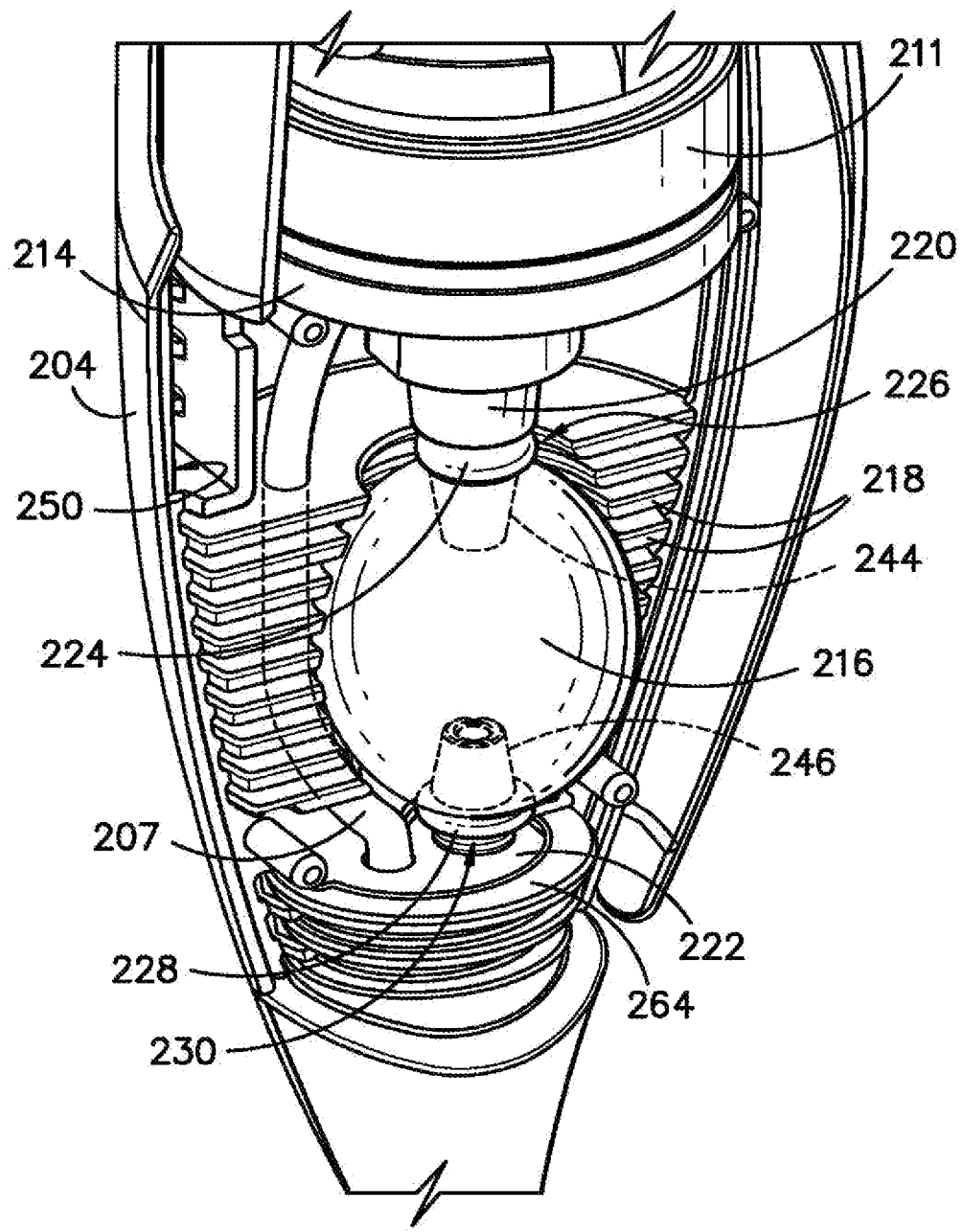
FIG. -7-

BOLUS DELIVERY DEVICE

CROSS-REFERENCE TO RELATED APPLICATIONS

This application is a continuation of U.S. application Ser. No. 16/618,583 filed Dec. 2, 2019 (now U.S. Pat. No. 11,273,254), the National Stage Entry of International Patent Application No. PCT/US2018/028112, filed Apr. 18, 2018, which claims priority to U.S. Provisional Application Ser. No. 62/516,165, filed on Jun. 7, 2017, the contents of which are incorporated herein by reference thereto.

FIELD

The present invention relates to fluid dispensing apparatus and pertains particularly to infusion assemblies having features for administering a bolus dose of fluid.

BACKGROUND

In instances of severe pain, infection, and other medical ailments, it has been proven beneficial to administer a continuous flow of medicinal fluid to a patient through a catheter-based system. There are many types of medicinal fluids that can be administered in this manner including, but not limited to, insulin, analgesics, and antibiotics. Often, patients are intravenously supplied with the medicinal fluid, e.g., a pharmaceutically active liquid, at a controlled rate over a long period of time. The medicinal fluid also may be delivered to a patient's intramuscular space. Preferably, such infusion is accomplished while the patient is in an ambulatory state. Typically, an infusion assembly includes an inflatable elastomeric pump forming a liquid container that is supported by a mandrel, as well as a flow control valve or device and tubing for supply of the liquid to the patient. The walls of the pump are forced to expand when filled with the liquid and provide pressure for expelling the liquid.

Some infusion assemblies include a device for providing a bolus of the medicinal fluid, often with patient or user operable actuators such that the patient or another user can initiate the administration of bolus doses. However, typical bolus delivery devices may not prevent over-filling of the bolus reservoir, which could lead to over-administration of the medication. Further, the bolus reservoir may leak fluid, which can affect the volume of the bolus dose, as well as can be messy and inconvenient for the user.

Accordingly, bolus delivery devices that include one or more safety mechanisms for preventing over-administration of medication, as well as one or more features for preventing leaks from the bolus reservoir, would be desirable. Infusion assemblies incorporating such improve bolus delivery devices also would be advantageous.

SUMMARY

Aspects and advantages of the invention will be set forth in part in the following description, or may be obvious from the description, or may be learned through practice of the invention.

In one aspect, the present subject matter is directed to a bolus delivery device. The bolus delivery device comprises a housing and a reservoir disposed within the housing for receipt of a volume of a fluid. The reservoir is defined by an activation dome and a reservoir seat. The bolus delivery device further comprises a bladder disposed in the housing. The bladder is in fluid communication with the reservoir for receipt of the fluid from the reservoir. The bolus delivery device also comprises an actuator; an inlet conduit in fluid communication with the reservoir for providing the fluid to the reservoir; and an outlet conduit in fluid communication with the bladder for providing the fluid to a patient. The actuator is in operative communication with the reservoir to initiate a flow of the fluid from the reservoir to the bladder. The bladder expands as the bladder receives the fluid and contracts as the bladder dispenses the fluid. It should be understood that the bolus delivery device may be further configured with any of the additional features as described herein.

In some embodiments, the reservoir seat is located between the activation dome and the bladder such that the reservoir seat is distal to the activation dome and proximal to the bladder. Also, the bolus delivery device may comprise a piston axially disposed within the reservoir and extending through an orifice in the reservoir seat, the piston having a proximal end and a distal end; a seal member disposed around the distal end of the piston and against a distal side of the orifice in the reservoir seat; and a biasing member disposed around the distal end of the piston. In such embodiments, the activation dome is connected to the actuator and the proximal end of the piston such that operating the actuator displaces the piston to displace the seal member and initiate the flow of fluid from the reservoir to the bladder. In some embodiments, the seal member is free to slide along the piston. Further, the reservoir has a fluid pressure that varies as the volume of the fluid varies within the reservoir, and the biasing member has a biasing force that overcomes the fluid pressure of the reservoir when the reservoir is substantially empty. Additionally, a collar may be disposed between the seal member and the biasing member, e.g., to more evenly distribute the pressure of the biasing member about the seal member to aid in the sealing force of the biasing member.

In some embodiments, the housing defines ribs that limit the expansion of the bladder. In still other embodiments, the inlet conduit is in fluid communication with an elastomeric pump. Moreover, the bladder may extend between a proximal connector and a distal connector, and in such embodiments, the inlet conduit is in fluid communication with the distal connector and the outlet conduit is in fluid communication with the distal connector. An O-ring may secure a proximal end of the bladder to the proximal connector and another O-ring may secure a distal end of the bladder to the distal connector. Further, the bolus delivery device may include an internal conduit extending from the distal connector to the reservoir. The internal conduit provides fluid communication between the inlet conduit and the reservoir.

In yet other embodiments, the bolus delivery device comprises a stop that catches in a groove defined in the actuator to limit the distal movement of the actuator. Additionally or alternatively, the actuator may be operable by the patient to initiate a release of fluid from the bolus delivery device to the patient. In such embodiments, the actuator is configured such that it requires minimal effort to force the fluid out of the bolus delivery device and that, when actuated by the patient, fluid is permitted to flow out of the bolus delivery device to the patient without further action by the patient. Further, the bolus delivery device also may comprise a removable tab that holds the actuator in a depressed position to self-prime the bolus delivery device.

In another aspect, the present subject matter is directed to an infusion assembly. The infusion assembly comprises an elastomeric pump configured to provide a fluid under pressure; a continuous flow path in fluid communication with the pump for providing a continuous and substantially constant flow rate of fluid from the pump; a bolus flow path for the delivery of a bolus dose of the fluid; and a bolus delivery device in fluid communication with the bolus flow path and configured to receive fluid from the pump. The bolus delivery device includes a housing and a reservoir disposed within the housing for receipt of a volume of a fluid. The reservoir is defined by an activation dome and a reservoir seat. The bolus delivery device further comprises a bladder disposed in the housing. The bladder is in fluid communication with the reservoir for receipt of the fluid from the reservoir. The bolus delivery device also comprises an actuator; an inlet conduit in fluid communication with the reservoir for providing the fluid to the reservoir; and an outlet conduit in fluid communication with the bladder for providing the fluid to a patient. The actuator is in operative communication with the reservoir to initiate a flow of the fluid from the reservoir to the bladder. The bladder expands as the bladder receives the fluid and contracts as the bladder dispenses the fluid. It should be understood that the infusion assembly may be further configured with any of the additional features as described herein.

In some embodiments, the pump provides the fluid under a pressure of up to about 30 psi. In other embodiments, the pump provides the fluid under a pressure within a range of about 10 psi to about 30 psi. In still other embodiments, the pump provides the fluid under a pressure within a range of about 15 psi to about 25 psi.

Moreover, in some embodiments, the reservoir seat is located between the activation dome and the bladder such that the reservoir seat is distal to the activation dome and proximal to the bladder. Also, the bolus delivery device of the infusion assembly may comprise a piston axially disposed within the reservoir and extending through an orifice in the reservoir seat, the piston having a proximal end and a distal end; a seal member disposed around the distal end of the piston and against a distal side of the orifice in the reservoir seat; and a biasing member disposed around the distal end of the piston. In such embodiments, the activation dome is connected to the actuator and the proximal end of the piston such that operating the actuator displaces the piston to displace the seal member and initiate the flow of fluid from the reservoir to the bladder. In some embodiments, the seal member is free to slide along the piston. Further, the reservoir has a fluid pressure that varies as the volume of the fluid varies within the reservoir, and the biasing member has a biasing force that overcomes the fluid pressure of the reservoir when the reservoir is substantially empty.

In some embodiments, the housing defines ribs that limit the expansion of the bladder. In still other embodiments, the inlet conduit is in fluid communication with an elastomeric pump. Moreover, the bladder may extend between a proximal connector and a distal connector, and in such embodiments, the inlet conduit is in fluid communication with the distal connector and the outlet conduit is in fluid communication with the distal connector. An O-ring may secure a proximal end of the bladder to the proximal connector and another O-ring may secure a distal end of the bladder to the distal connector. Further, the bolus delivery device of the infusion assembly may include an internal conduit extending from the distal connector to the reservoir. The internal conduit provides fluid communication between the inlet conduit and the reservoir.

In yet other embodiments, the bolus delivery device of the infusion assembly comprises a stop that catches in a groove defined in the actuator to limit the distal movement of the actuator. Additionally or alternatively, the actuator may be operable by the patient to initiate a release of fluid from the bolus delivery device to the patient. In such embodiments, the actuator is configured such that it requires minimal effort to force the fluid out of the bolus delivery device and that, when actuated by the patient, fluid is permitted to flow out of the bolus delivery device to the patient without further action by the patient. Further, the bolus delivery device of the infusion assembly also may comprise a removable tab that holds the actuator in a depressed position to self-prime the bolus delivery device.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 is a schematic view of an infusion assembly having a bolus delivery device according to an exemplary embodiment of the present subject matter.

FIG. 2 is a side perspective view of the bolus delivery device of FIG. 1.

FIG. 3A is a side view of the bolus delivery device of FIG. 1 with a portion of a housing of the device removed and with a tab installed to depress an actuator of the device for self-priming the device.

FIG. 3B is the side view of FIG. 3A with the tab removed.

FIG. 3C is the side view of FIG. 3B with compression collar of the device shown as transparent, rather than as opaque as in FIG. 3B.

FIG. 4 is an axial cross-section view of the bolus delivery device of FIG. 1, with a reservoir of the device at its maximum volume and a bladder of the device in a fully relaxed state.

FIG. 5 is an axial cross-section view of the bolus delivery device of FIG. 1, with a reservoir of the device at its minimum volume and a bladder of the device in a fully expanded state.

FIG. 6 is a close-up view of a distal portion of the bolus delivery device of FIG. 4.

FIG. 7 is a close-up view of a distal portion of the bolus delivery device of FIG. 5.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Moreover, the particular naming of the components, capitalization of terms, the attributes, data structures, or any other programming or structural aspect is not mandatory or significant, and the mechanisms that implement the invention or its features may have different names, formats, or protocols. Also, the particular division of functionality between the various components described herein is merely exemplary and not mandatory; functions performed by a single component may instead be performed by multiple components, and functions performed by multiple components may instead performed by a single component.

Further, the detailed description uses numerical and letter designations to refer to features in the drawings. Like or similar designations in the drawings and description have been used to refer to like or similar parts of the invention. As used herein, the terms "first," "second," and "third" may be used interchangeably to distinguish one component from another and are not intended to signify location or importance of the individual components.

Referring to the drawings, FIG. 1 provides a side view of an infusion assembly, e.g., for dispensing a fluid to a patient, according to an exemplary embodiment of the present subject matter. As shown, the exemplary infusion assembly 100 includes an elastomeric pump 102 having an upper support member 104 and a lower support member 106. Infusion assembly 100 defines an axial direction A, and lower support member 106 is spaced apart from upper support member 104 along the axial direction A.

More particularly, pump 102 defines a reservoir that serves as a pressurized fluid source, holding medicinal fluid, such as local anesthetics, and providing a source of fluid under pressure. Pump 102 forces the medicinal fluid through a tubing or conduit 108. Conduit 108 forms a continuous flow path 110 for delivery of the medicinal fluid into a wound site nerve bundle or the blood stream of a patient P. In the depicted exemplary embodiment, conduit or tubing 108 defines an outlet 112 connecting the continuous flow path 110 to a catheter 114 that delivers the medicinal fluid to patient P. In such embodiments, conduit 108 and catheter 114 may together define continuous flow path 110 from pump 102 to patient P.

Further, in some embodiments, infusion assembly 100 may be configured to provide for bolus delivery. In such configurations, conduit 108 may split into a continuous or primary flow path 110 and a controlled bolus flow path 140. Thus, medicinal fluid may be delivered into a wound site nerve bundle or the blood stream of patient P from pump 102 via the continuous or primary flow path or from a bolus delivery device 200 via the controlled bolus flow path. The bolus delivery device 200 is described in greater detail below.

Pump 102 preferably accommodates a volume from about 100 to 500 ml of fluid under a pressure of up to approximately 30 psi. In some embodiments, the pump may hold the fluid under a pressure of about 10 psi to about 30 psi and, in other embodiments, under a pressure of about 15 psi to about 25 psi. More particularly, pump 102 has an inner core 116 extending between upper support member 104 and lower support member 106 along axial direction A. Inner core 116 is surrounded by an elastomeric bladder 118 within a housing 120. Inner core 114 preferably has an inlet port 122, e.g., to fill bladder 118 with fluid, and an outlet port 124 in fluid communication with conduit 108, e.g., to dispense the fluid from bladder 118 to patient P through flow path 110. Fluid is held under pressure within elastomeric bladder 118 and flows from elastomeric bladder 118 into conduit 108 through outlet port 124, preferably flowing at a controlled and predictable rate. Alternatively, conduit 108 may be sized to serve as a flow restrictor. Further, elastomeric bladder 118 preferably is constructed from a resilient material that may comprise a variety of elastomeric compositions well known in the art, including vulcanized synthetic polyisoprenes, natural latex, natural rubber, synthetic rubber, silicone rubber, or the like.

Exemplary pumps are described in U.S. Pat. Nos. 7,959,623 and 5,254,481, which are hereby incorporated by reference. A variety of other conventional pumps also may be used. For example, the pumps described in U.S. Pat. Nos. 5,080,652 and 5,105,983, which are hereby incorporated by reference, may be used. As will be understood by those of skill in the art, other suitable electronic or mechanical pumps offered by other manufacturers may be used as well.

Continuing with FIG. 1, an optional clamp 126 is positioned in flow path 110 downstream from pump 102. Clamp 126 can compress conduit 108 such that fluid flow from pump 102 through flow path 110 is occluded. Such occlusion is advantageous, e.g., for the transportation and preparation of infusion assembly 100 as described herein. An exemplary clamp 126 is described in U.S. Pat. No. 6,350,253, which is hereby incorporated by reference. However, a variety of other conventional clamps known in the industry may be used to occlude the flow of fluid from pump 102 through flow path 110, such as compression clamps, C clamps, roller clamps, and the like.

An optional filter 128 downstream of clamp 126 separates the fluid from contaminates and other undesired particles that may be found within the fluid. Filter 128 also preferably eliminates air from fluid flow path 110. One such filter 128 is described in U.S. Pat. No. 6,350,253, which is hereby incorporated by reference. Of course, other suitable filters recognized in the industry may be used to capture undesired particles and/or remove air from the system.

As further shown in FIG. 1, an optional flow regulator 130 is positioned in continuous flow path 110. Flow regulator 130 sets the continuous and substantially constant flow rate of fluid from pump 102 to patient P via tubing 108. In some embodiments, the flow rate may be adjusted to a rate within a range, e.g., within a range of about 0.5 to about 14 cubic centimeters of fluid per hour. Flow regulator 130 may be manually adjustable, if desired, and provided with a dial, switch, or lever with an adjustable flow rate control display corresponding to the range of flow rates. For example, the flow rate range may be from about 1 to about 7 or from about 2 to about 14 cubic centimeters of fluid per hour such that the flow rate control display includes a lowermost value of 1 and an uppermost value of 7 or a lowermost value of 2 and an uppermost value of 14. It will be appreciated that the foregoing flow rate values are only exemplary, and in other embodiments, infusion assembly 100 may have other flow rates and the flow rate may be adjustable within another range of flow rates. Alternatively, a constant flow regulator (i.e., a regulator that is not adjustable) can be employed. For example, an optional flow regulating orifice, such as a glass orifice tube 132, may be employed in the primary or continuous flow path 110. Moreover, in embodiments having a bolus flow path, an optional second flow regulating orifice 146 may be employed in the bolus flow path.

The particular arrangement of clamp 126, filter 128, and flow regulator 130 (or glass tube 132) described herein is merely exemplary. These elements, if present, may be arranged in any order, as will be easily understood by those skilled in the art. Desirably, however, glass orifice tube 132 is located downstream of filter 128 when orifice tube 132 and filter 128 are provided in infusion assembly 100.

In the exemplary embodiment illustrated in FIG. 1, the conduit 108 splits into two flow paths, the continuous or primary flow path 110 and the bolus flow path 140. A bolus delivery device 200 is in fluid communication with the bolus flow path 140. The bolus delivery device 200 accumulates a quantity of fluid from the bolus flow path 140 leading from the pump 102 and holds the fluid under pressure until the bolus dose is triggered by a patient operable actuator 202 for release into the patient P. Generally, the bolus delivery device 200 is configured to receive fluid, elastically expand to pressurize the fluid, store the pressurized fluid, and dispense the pressurized fluid while avoiding over-administration of a medicinal fluid to the patient. Downstream from the bolus delivery device 200, the continuous flow path 110 and the bolus flow path 140 converge into a single flow path. Optionally, a clamp 142, a filter 144, and/or a flow regulating orifice 146 may be positioned in the bolus flow path 140. The clamp 142 can compress the flow path 140 such that fluid flow from the pump 102 is occluded. Such occlusion is advantageous, e.g., for the transportation and preparation of the fluid delivery device. Further, although described herein as a patient operable bolus delivery device 200, it will be appreciated that any user, such as the patient P, a caregiver, a physician, etc., may operate the actuator 202 to dispense a bolus dose of the medicinal fluid to the patient P.

Turning now to FIGS. 2-7, the bolus delivery device 200 will be described in greater detail. As shown in FIG. 2, the bolus delivery device 200 comprises a housing 204 that supports the actuator 202. As previously described, the actuator 202, configured as a depressible button in the illustrated exemplary embodiment, may be operated by the patient P to dispense a bolus dose of medicinal fluid from the bolus delivery device 200. Further, an inlet conduit 206 provides fluid from the bolus flow path 140 to the bolus delivery device 200, such that the inlet conduit 206 is in fluid communication with the pump 102, and an outlet conduit 208 delivers fluid from the bolus delivery device 200 to the bolus flow path for delivery to the patient.

In addition, the exemplary bolus delivery device 200 includes features for self-priming the device. FIG. 3A provides a side view of the bolus delivery device 200, with a portion of the housing 204 removed to illustrate the internal configuration of the device 200. As illustrated in FIGS. 2 and 3A, during assembly of the device 200, a removable tab 203 is installed that keeps or holds the actuator 202 in a depressed or activated position. With the actuator 202 depressed by the tab 203 when the device 200 is first placed in fluid communication with the pump 102, fluid from the pump flows through the bolus delivery device 200, including through a reservoir 210 disposed within the housing 204 for receipt of a volume of fluid from the pump 102. As such, the fluid displaces the air within the device 200. Once the fluid has flowed through the device 200, the tab 203 may be removed, and the actuator 202 moves to a extended or non-depressed position as the fluid fills the reservoir 210 of the device 200 (as described in greater detail below) and the fluid pressure within the device increases.

FIG. 3B provides the side view of FIG. 3A with the tab 203 removed. FIG. 3C provides the same side view as FIG. 3B but with a compression collar of the device shown as transparent, rather than as opaque as in FIG. 3B. As shown in FIGS. 3A, 3B, and 3C, the activation dome 212 and a reservoir seat 214 together define the reservoir 210, i.e., a cavity for receipt of a bolus volume of fluid from the pump 102. The inlet conduit 206 is in fluid communication with the reservoir 210 for providing the fluid to the reservoir. Further, the activation dome 212 and the reservoir seat 214 have suitable dimensions and material properties to limit their expansion and thereby limit the bolus volume of reservoir 210 to a reliable, repeatable, and desirable volume of fluid.

A bladder 216 is disposed in the housing 204 distal to the reservoir 210. The bladder 216 is in fluid communication with the reservoir 210 for receipt of the fluid from the reservoir, and the bladder 216 is in fluid communication with the outlet conduit 208 for providing the fluid to the patient P. More particularly, as shown in FIGS. 3A, 3B, and 3C, the actuator 202 is disposed proximal to the reservoir 210 such that when the actuator 202 is actuated, e.g., when the button is depressed by the patient P, the fluid accumulated in the reservoir 210 flows from the reservoir to the bladder 216. That is, the actuator 202 is in operative communication with the reservoir 210 to initiate a flow of the fluid from the reservoir 210 to the bladder 216. As the fluid flows into the bladder 216, the bladder expands to accommodate the fluid, and as described in greater detail below, the bladder 216 contracts to dispense the fluid from the bladder into the outlet conduit 208, through which the fluid ultimately flows to the patient P. The bladder 216 may be formed from an elastomer or other suitable material such that the bladder 216 is an expandable bladder. Further, the housing 204 includes internal ribs 218 that limit the expansion of the bladder 216, as will be described in more detail herein.

As also illustrated in FIGS. 3A, 3B, and 3C, the reservoir seat 214 is located between the activation dome 212 and the bladder 216 such that the reservoir seat 214 is distal to the activation dome 212 and proximal to the bladder 216. Further, the bladder 216 extends between a proximal connector 220 and a distal connector 222. As such, the proximal connector 220 is disposed between the reservoir seat 214 and the bladder 216. The inlet conduit 206 and the outlet conduit 208 are each in fluid communication with the distal connector 222, which may be configured as a distal manifold 222. The flow regulating orifice 146 (FIG. 1) may be disposed within the inlet conduit 206, e.g., to help control the refill rate of the bolus delivery device 200. An internal conduit 207 extends from the distal connector 222 to the reservoir 210 to provide the fluid to the reservoir 210. In some embodiments, the flow regulating orifice is made from glass, but in other embodiments, the flow regulating orifice is made from any suitable flexible material. Other materials also may be used to form the flow regulating orifice 146.

The reservoir 210 provides the fluid to the bladder 216 through the proximal connector 220, and the bladder 216 provides the fluid to the outlet conduit 208 through the distal connector 222. An O-ring 224, or other suitable seal or securement member, secures a proximal end 226 of the bladder 216 to the proximal connector 220. Similarly, an O-ring 228, or other suitable seal or securement member, secures a distal end 230 of the bladder 216 to the distal connector 222. In the depicted embodiment, the housing 204 also includes a clip 205, or other suitable attachment member, e.g., for attaching the bolus delivery device 200 to the patient's clothing or other support.

Referring to FIGS. 4 and 5, cross-section views of the bolus delivery device 200 are provided that help illustrate the operation of the device 200. In FIG. 4, the actuator 202 is at its most proximal position, i.e., the actuator 202 is not actuated or depressed. Further, the reservoir 210 is at its maximum volume, which is limited by a compression collar 211 (further described below), the activation dome 212 and reservoir seat 214, and the bladder 216 is in a fully relaxed state. In FIG. 5, the actuator is at its most distal position, i.e., the actuator 202 is actuated or depressed to initiate a bolus dose of medicinal fluid to the patient. Additionally, the reservoir 210 is at its minimum volume, and the bladder 216 is in a fully expanded state. The actuator 202 is configured such that it requires minimal effort to force the fluid out of the reservoir 210 and that, when actuated by the patient P, fluid is permitted to flow out of the reservoir 210 to the patient without further action by the patient. More particularly, fluid from the pump 102 is stored in the reservoir 210 until the patient P is ready for a bolus, and the bolus delivery device 200 prevents flow from the reservoir 210 until a bolus is desired. A piston 232 is axially disposed within the reservoir 210 and through an orifice 234 in the reservoir seat 214. The activation dome 212 is connected to the actuator 202 and a proximal end 239 of the piston 232 via an interference fit. Further, a seal member, such as O-ring 236, and a biasing member, such as spring 238, are disposed around a distal end 240 of the piston 232, within a channel 215 defined in the reservoir seat 214. The O-ring 236 is disposed against a distal side 242 of the orifice 234 in the reservoir seat 214, which creates a seal that prevents flow from the reservoir 210 into the bladder 216. In other embodiments, other suitable seal members 236 may be used to seal the distal side 242 of the orifice 234, i.e., in addition to or as an alternative to O-ring 236. Moreover, other suitable biasing members 238 may be used in place of or in addition to spring 238. It will be appreciated that the biasing member 238 has a biasing force, e.g., the spring 238 has a spring force. In some embodiments, a collar 237 is inserted between the seal member 236 and the biasing member 238. The collar 237 may be a castle washer or the like; a castle washer has ridge-like features along its top end that resemble a castle tower. The biasing member 238 interfaces with a bottom end of the collar 237, and the top end of the collar 237 interfaces with a bottom surface of the seal member 236, distributing the pressure of the biasing member 238 around the seal member 236 to aid in the sealing force provided by the seal member 236 and biasing member 238. In embodiments in which the collar 237 is a castle washer, the ridges of the castle washer 237 help evenly distribute the pressure of the biasing member 238 around the seal member 236, as well as allow liquid to evacuate the area quickly.

As shown in FIG. 4, when the activation dome 212 is in its fully expanded state, the piston 232 pulls the O-ring 236 against the reservoir seat 214. After the reservoir 210 is filled, the patient P pushes down on the actuator 202 to dispense the bolus. As shown in FIG. 5, when the patient P operates or depresses the actuator 202, the actuator 202 compresses the activation dome 212 and displaces the piston 232. When displaced or extended into the reservoir seat 214, the piston 232 does not pull the O-ring 236. Rather, the spring 238 pushes the O-ring 236 against the reservoir seat 214 and the O-ring 236 is held in place only by the spring 238. The O-ring 236 is free to slide along the piston 232, and the spring 238 does not interfere with the movement of the piston 232. The fluid pressure from the compressed activation dome 212 overcomes the force of the spring 238 and pushes the O-ring 236 away from the reservoir seat orifice 234. Fluid moves past the O-ring 236 through the reservoir seat 214 and into the bladder 216 through the proximal connector 220, which connects the bladder 216 to the reservoir seat 214.

The volume of the reservoir 210 is greater than the internal volume of the bladder 216 in its relaxed state. The bladder 216 expands to accommodate the bolus volume, acting as work storage and eliminating the need for the patient to hold down or continuously actuate the actuator 202 to dispense the bolus dose. That is, the bladder 216 stores energy to dispense the bolus automatically. The contraction of the bladder 216 forces the fluid through the distal connector 222 into the outlet conduit 208 and, ultimately, to the patient P.

The reservoir 210 has a fluid pressure that varies as the volume of fluid varies within the reservoir. After the fluid moves from the reservoir 210 to the bladder 216, the fluid pressure inside the reservoir 210 is no longer sufficient to overcome the spring force of spring 238 or, more generally, the biasing force of the biasing member 238. Stated differently, the biasing force overcomes the fluid pressure of the reservoir 210 when the reservoir is substantially empty. Accordingly, the spring 238 extends and pushes the O-ring 236 against the distal side 242 of the reservoir seat orifice 234. The seal between the piston 232, reservoir seat 214, and the O-ring 234 prevents flow from the expanded bladder 216 back into the activation dome 212. Fluid from the pump 102 refills the reservoir 210, expanding the activation dome 212 and gradually returning the piston 232 to its original position. However, the patient P can actuate or depress the actuator 202 at any time and receive a partial bolus dose. There is no lockout mechanism to prevent a partial bolus while the reservoir 210 is in a refill state. Nonetheless, as described below, the bolus delivery device 200 incorporates features for preventing over-administration of medication, e.g., through a larger bolus dose than the maximum expanded volume of the bladder 216.

The piston 232 prevents leakage past the sealing O-ring 236 and thereby prevents leakage within or internal to the bolus delivery device 200. As the reservoir 210 fills, the internal pressure increases to match that of the elastomeric pump 102, i.e., the fluid source. Increased pressure in the reservoir 210 expands the activation dome 212, which pulls the piston 232 against the sealing O-ring 236, increasing the sealing force against the reservoir seat 214. The configuration of the activation dome 212, the piston 232, and the O-ring 236 ensures the device 200 operates in a wider pressure range, e.g., up to about 30 psi, to accommodate different sizes of the pump 102.

Turning now to FIGS. 6 and 7, the internal configuration of the bolus delivery device 200 in the vicinity of the bladder 216 will be described in greater detail. FIG. 6 provides a cross-section view of the distal portion of the device 200 with the bladder 216 in its fully relaxed or contracted state. FIG. 7 provides a cross-section view of the distal portion of the device 200 with the bladder 216 in its fully expanded state. As illustrated in FIG. 7, the proximal connector 220 includes an outlet 244 that extends into the bladder 216. The O-ring 224 secures the proximal end 226 of the bladder 216 to the outlet 244. Moreover, the distal connector 222 includes an inlet 246 that extends into the bladder 216. The O-ring 228 secures the distal end 230 of the bladder 216 to the inlet 246. Fluid from the reservoir 210 is provided through the outlet 244, and the fluid egresses from or exits the bladder 216 to flow to the patient through the inlet 246. As also illustrated in FIGS. 6 and 7, the internal conduit 207 extends directly to the reservoir 210, i.e., to the activation dome 212 or the reservoir seat 214, to provide fluid from the pump 102 to the reservoir 210.

Further, as shown in the depicted embodiment, the housing 204 defines ribs 218 along an internal surface 250 of the housing 204. As illustrated most clearly in FIG. 7, the ribs 218 constrain the expanded state of the bladder 216 to a desirable volume. Thus, in the event that the bladder 216 cannot empty and return to its contracted state, e.g., an occlusion in the outlet conduit 208 or a distal component prevents the bladder 216 from dispensing the fluid, the reservoir 210 will continue to refill but the patient P will be unable to actuate or depress the actuator 202. More specifically, the bladder 216 will not accommodate any additional fluid in its fully expanded state and, therefore, the activation dome 212 cannot be compressed. Accordingly, a larger bolus dose cannot be administered, i.e., the ribs 218 of housing 204 constrain the expansion of bladder 216 to prevent over-administration of medication.

Moreover, the housing 204 includes features at a proximal portion of the device 200 that work with the activation dome 212 to control bolus volume. For instance, features within the housing 204 constrain the movement of the actuator 202 and the activation dome 212. More particularly, when the reservoir 210 is full, the activation dome 212 reaches a final expanded volume that is limited by a compression collar 211 that extends about the activation dome 212. For instance, the activation dome 212 may be made from a material such as silicone that could over-inflate if not limited by a feature such as the compression collar 211. Further, in some embodiments, the physical dimensions of the actuator 202 and housing 204, as well as the seal created by the piston 232, spring 238, and O-ring 236 assembly, also may limit the expansion of the activation dome 212. These constraints help prevent over-expansion of the activation dome 212, such that the activation dome 212 cannot expand beyond a pre-determined maximum volume.

Additionally, referring back to FIGS. 4 and 5, a stop 252 limits the distal movement of the actuator 202, and the reservoir seat 214 limits the distal movement of the activation dome 212. More specifically, the actuator 202 includes a guide extension 254 that moves distally and proximally within a guide slot 256 defined by the housing 204. The movement of the guide extension 254 within the guide slot 256 helps ensure the stop 252 catches or seats within a groove 258 defined in the actuator 202 to stop, and thereby constrain, the distal movement of the actuator 202 in a fully actuated or fully depressed state, shown in FIG. 5. Moreover, when the actuator 202 is fully actuated or depressed, the activation dome 212 is collapsed against the reservoir seat 214. The actuator 202 includes a distal end 260 that presses the activation dome 212 against an internal surface 262 of the reservoir seat 214. As illustrated in FIG. 5, the distal end 260 of the actuator 202 generally is shaped complementarily to the internal surface 262 of the reservoir seat 214 such that the activation dome 212 generally conforms to the shape of the reservoir seat internal surface 262 when the activation dome 212 is substantially collapsed and reservoir 210 is substantially empty.

The housing 204 may also include one or more features for minimizing stresses on various components within the bolus delivery device 200. For example, referring back to FIGS. 3B and 3C, a strain relief 264 may be used at the distal connector 222 to minimize the stress to the inlet conduit 206, internal conduit 207, and/or outlet conduit 208, which are all connected to the distal connector 222. As shown in FIGS. 3B and 3C, the strain relief 264 includes two or more ridges 266 that help relieve the stress on the conduits 206, 207, 208. The housing 204 also may incorporate other features for reducing and/or eliminating stress on other components of the bolus delivery device 200.

Accordingly, it will be appreciated that the release rate of the bolus dose of the fluid to the patient P is controlled by at least in part by the decompression of the bladder 216. Other features of the infusion assembly 100 downstream of the bolus delivery device 200, such as the diameter of the catheter 114, may also control the release rate of the fluid to the patient P. Advantageously, the patient P does not have to provide pressure to force fluid out of the bolus delivery device 200 into the bolus flow path 140. Rather, the patient P can simply actuate or depress the actuator 202 to administer the bolus dose. If the patient P activates or operates the actuator 202 prior to the time the bolus reservoir 210 has filled to its capacity, the patient P receives less than the full amount of the bolus dose. In effect, this prevents the patient P from self-administering more than the maximum desired amount of fluid per the time specified as a bolus dose.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include so structural elements that do not differ from the literal language of the claims or if they include equivalent structural elements with insubstantial differences from the literal language of the claims.

What is claimed is:

1. A bolus delivery device comprising:
   a housing;
   a reservoir disposed within the housing for receipt of a volume of a fluid, the reservoir defined by an activation dome and a reservoir seat, the reservoir having a fluid pressure that varies as the volume of the fluid varies within the reservoir;
   a piston axially disposed within the reservoir and extending through an orifice in the reservoir seat, the piston having a proximal end and a distal end;
   a biasing member disposed around the distal end of the piston;
   a seal member disposed around the distal end of the piston and against a distal side of the orifice in the reservoir seat;
   an expandable bladder disposed in the housing, the expandable bladder in fluid communication with the reservoir for receipt of the fluid from the reservoir;
   an actuator for initiating a flow of the fluid from the reservoir to the expandable bladder;
   an inlet conduit in fluid communication with the reservoir for providing the fluid to the reservoir; and
   an outlet conduit in fluid communication with the expandable bladder for providing the fluid to a patient,
   wherein the biasing member has a biasing force that overcomes the fluid pressure of the reservoir when the reservoir is substantially empty to push the seal member against the distal side of the reservoir seat.

2. The bolus delivery device of claim 1, wherein the reservoir seat is located between the activation dome and the expandable bladder such that the reservoir seat is distal to the activation dome and proximal to the expandable bladder.

3. The bolus delivery device of claim 1, wherein the activation dome is connected to the actuator and the proximal end of the piston such that operating the actuator displaces the piston to displace the seal member and initiate the flow of fluid from the reservoir to the expandable bladder.

4. The bolus delivery device of claim 1, wherein the seal member is free to slide along the piston.

5. The bolus delivery device of claim 1, wherein the expandable bladder expands as the fluid is received and contracts as the fluid is dispensed.

6. The bolus delivery device of claim 1, further comprising a collar disposed between the seal member and the biasing member.

7. The bolus delivery device of claim 1, wherein the housing defines ribs that limit expansion of the expandable bladder.

8. The bolus delivery device of claim 1, wherein the expandable bladder extends between a proximal connector and a distal connector, and wherein the inlet conduit is in fluid communication with the distal connector and the outlet conduit is in fluid communication with the distal connector.

9. The bolus delivery device of claim 1, further comprising a stop that catches in a groove defined in the actuator to limit distal movement of the actuator.

10. The bolus delivery device of claim 8, further comprising an internal conduit extending from the distal connector to the reservoir, the internal conduit providing fluid communication between the inlet conduit and the reservoir.

11. A bolus delivery device comprising:
a housing;
a reservoir disposed within the housing for receipt of a volume of a fluid, the reservoir defined by an activation dome and a reservoir seat;
a piston axially disposed within the reservoir and extending through an orifice in the reservoir seat, the piston having a proximal end and a distal end;
a seal member disposed around the distal end of the piston and against a distal side of the orifice in the reservoir seat, wherein the seal member is free to slide along the piston;
a bladder disposed in the housing and in fluid communication with the reservoir for receipt of the fluid from the reservoir, wherein the bladder expands as the fluid is received and contracts as the fluid is dispensed; and
an actuator for initiating a flow of the fluid from the reservoir to the bladder.

12. The bolus delivery device of claim 11, wherein the reservoir seat is located between the activation dome and the bladder such that the reservoir seat is distal to the activation dome and proximal to the bladder.

13. The bolus delivery device of claim 11, further comprising a biasing member disposed around the distal end of the piston, wherein the activation dome is connected to the actuator and the proximal end of the piston such that operating the actuator displaces the piston to displace the seal member and initiate the flow of fluid from the reservoir to the bladder.

14. The bolus delivery device of claim 11, wherein the housing defines ribs that limit expansion of the bladder.

15. The bolus delivery device of claim 11, further comprising:
an inlet conduit in fluid communication with the reservoir for providing the fluid to the reservoir; and
an outlet conduit in fluid communication with the bladder for providing the fluid to a patient.

16. The bolus delivery device of claim 13, wherein the reservoir has a fluid pressure that varies as the volume of the fluid varies within the reservoir, and wherein the biasing member has a biasing force that overcomes the fluid pressure of the reservoir when the reservoir is substantially empty to push the seal member against the distal side of the reservoir seat.

17. The bolus delivery device of claim 13, further comprising a collar disposed between the seal member and the biasing member.

18. The bolus delivery device of claim 15, wherein the bladder extends between a proximal connector and a distal connector, and wherein the inlet conduit is in fluid communication with the distal connector and the outlet conduit is in fluid communication with the distal connector.

19. The bolus delivery device of claim 18, further comprising an internal conduit extending from the distal connector to the reservoir, the internal conduit providing fluid communication between the inlet conduit and the reservoir.

20. An infusion assembly comprising:
an elastomeric pump configured to provide a fluid under pressure;
a continuous flow path in fluid communication with the pump for providing a continuous and substantially constant flow rate of fluid from the pump;
a bolus flow path for delivery of a bolus dose of the fluid; and
a bolus delivery device in fluid communication with the bolus flow path and configured to receive fluid from the pump, the bolus delivery device including:
a housing;
a reservoir disposed within the housing for receipt of a volume of a fluid, the reservoir defined by an activation dome and a reservoir seat, the reservoir having a fluid pressure that varies as the volume of the fluid varies within the reservoir;
a piston axially disposed within the reservoir and extending through an orifice in the reservoir seat, the piston having a proximal end and a distal end;
a biasing member disposed around the distal end of the piston;
a seal member disposed around the distal end of the piston and against a distal side of the orifice in the reservoir seat;
an expandable bladder disposed in the housing, the expandable bladder in fluid communication with the reservoir for receipt of the fluid from the reservoir;
an actuator for initiating a flow of the fluid from the reservoir to the expandable bladder;
an inlet conduit in fluid communication with the reservoir for providing the fluid to the reservoir; and
an outlet conduit in fluid communication with the expandable bladder for providing the fluid to a patient,
wherein the biasing member has a biasing force that overcomes the fluid pressure of the reservoir when the reservoir is substantially empty to push the seal member against the distal side of the reservoir seat.

* * * * *